United States Patent [19]

Chazov et al.

[11] Patent Number: 4,695,622
[45] Date of Patent: Sep. 22, 1987

[54] HEXAPEPTIDE

[75] Inventors: Evgeny I. Chazov; Vladimir N. Smirnov; Valentin A. Vinogradov; Mikhail I. Titov; Vladimir A. Penin; Alexandr K. Giorgadze; Galina P. Titova; Zhanna D. Bespalova; Boris L. Pekelis; Nikolai K. Permyakov; Sergei I. Emelyanov; Alexandr A. Dzhikia, all of Moscow, U.S.S.R.

[73] Assignee: Vsesojuzny Kardiologichesky Nauchny Tsentr Akademii Meditsinskikh Nauk SSSR, Moscow, U.S.S.R.

[21] Appl. No.: 830,588
[22] PCT Filed: Apr. 24, 1987
[86] PCT No.: PCT/SU85/00032
 § 371 Date: Feb. 5, 1986
 § 102(e) Date: Feb. 5, 1986
[87] PCT Pub. No.: WO 86/00622
 PCT Pub. Date: Jan. 30, 1986

[30] Foreign Application Priority Data

Jul. 16, 1984 [SU] U.S.S.R. .............................. 3772995

[51] Int. Cl.$^4$ ............................................. C07K 7/06
[52] U.S. Cl. ................................................. 530/329
[58] Field of Search ........................................ 530/329

[56] References Cited

PUBLICATIONS

Article: Assessment of Antienzymatid Therapy of Destructive Pancreatitis, Yu A. Nesterenko, Yu P. Atano.

*Primary Examiner*—Delbert R. Phillips
*Attorney, Agent, or Firm*—Ladas & Parry

[57] ABSTRACT

A novel hexapeptide having the following structure:

Tyr-Ala-Gly-Phe-Leu-Arg.

The hexapeptide according to the present invention possesses an antipancreonecrotic activity.

1 Claim, 1 Drawing Figure

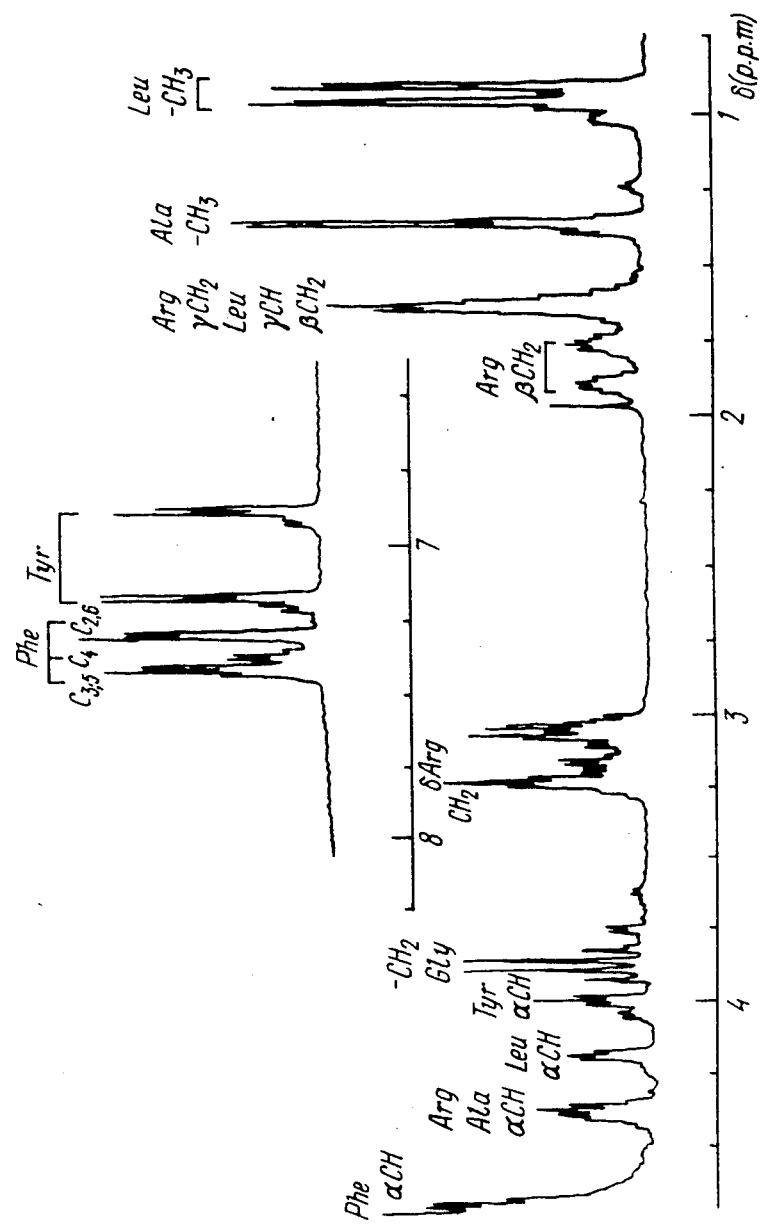

HEXAPEPTIDE

FIELD OF THE INVENTION

The present invention relates to the art of organic chemistry and, more particularly, to a novel hexapeptide.

STATE OF ART

At the present time acute pancreatitis is one of the most widespread diseases of the abdominal cavity organs. Parallel to the increasing general number of patients with acute pancreatitis, frequency of destructive forms of the disease is also growing. Despite the achieved success in the treatment of acute pancreatitis, hitherto in the case of a progressive necrosis of pancreas lethality remains high and reaches 50-60% on the average.

Known in the art are substances of a peptide nature such as glucagon and somatistatin inhibiting the external secretion of pancreas. (Greutzfeldt W. Gastrointestinal peptides: role in pathophysiology and diseases. Scand J. Gastroenterol., 1982 Suppl. 77, p. 7-20; Arnold R., Lankisch P. G. Somatostatin and the gastrointestinal tract, Glin. Gastroenterol., 1980, v. 9, p. 733-353).

However, these peptides proved to be less effective in the treatment of acute pancreatitis.

Known are carbasates of peptides which are selective inhibitors of elastase (cf. U.S. Pat. Nos. 4,064,236; 4,029,772 Cl. 424/177). However, this property of the compounds is not decisive in the treatment of acute pancreatitis, wherefore these substances have not enjoyed a wide clinical application.

At the present time for the treatment of acute pancreatitis antienzymatic preparations such as tracilol are used. However, these preparations are effective enough only in the case of an edematic (light) form of the diseases (cf. Nesterenko Yu. A., atanov Yu. P. Assessment of Antienzymatic Therapy of Destructive Pancreatitis, "Khirurgiya". 1981, No. 1, p. 84-88).

Basic preparations employed for the treatment of pancreatitis are cytostatics, for example 5-fluorouracyl (Laptev V. V. Treatment of Destructive Pancreatitis with 5)Fluorouracyl, "Khirurgiya", 1981, No. 1, p. 67-72). However, the use of cytostatics appears to be insufficiently effective; moreover, it is accompanied by undesirable side effects such as inhibition of processes of homopoiesis and suppression of immune reactions.

Known in the art are hexapeptides of various structures such as a hexapeptide His-D-Trp-Ala-Trp-D-Phe-Lys-NH$_2$ (Bowers C. Y. et al, Endocrinology, 1984, 114, No. 5, p. 1537-1545) or Tyr-D-Ala-Gly-Phe-Leu-Arg and the like (A. V. Waldman, O. S. Medvedev, Theoretical Prerequisits for Finding Novel Cardio-Vascular Agents Among Peptides, "Vestnik Akademii Meditsinskikh Nauk SSSR" (Newsletters of the USSR Academy of Medical Sciences), 1982, No. 5, p. 14-23).

However, an antipancreonecrotic activity for such compounds has been hitherto unknown.

DISCLOSURE OF THE INVENTION

The hexapeptide according to the present invention is novel and hitherto unknown from the literature.

The present invention is directed to the provision of a novel hexapeptide possessing a high antipancreonecrotic activity causing no side responses and useful in medicine.

This object has been accomplished by that a novel hexapeptide according to the present invention has the following structure: Tyr-Ala-Gly-Phe-Leu-Arg The hexapeptide according to the present invention comprises a white powder, well soluble in distilled water, a physiological solution, ethanol; insoluble in ether, ethylacetate, benzene. The melting temperature is 173°-176° C. $[\alpha]_D^{22} = -19.1$ (c 0.33 H$_2$O).

BEST MODE FOR CARRYING OUT THE INVENTION

The biological activity of the hexapeptide according to the present invention has been studied in experiments on dogs using an experimental acute pancreatitis model.

To this end, a similar operation was performed on 10 dogs. Under hexenal narcosis upper-median laparotomy was made. Into the wound a loop of duodenum was introduced with pancreas, cannulated and Wirsung's duct was dressed on a drain Snatorini's duct was additionally dressed too. Then the gall-bladder was punctured, bile was extracted therefrom and injected under pressure into Wirsung's duct at the rate of 0.5 ml per kg of the animal's bodyweight. As a stimulant of the pancreas secretion secretin and cholecystopancreoziimin were used which were intravenously administered at the rate of two units per kg of a dog's bodyweight. For administration of the stimulants of the pancreatic secretion, the hexapeptide according to the present invention and obtaining blood, the femoral vein was catheterized. For the measurement of diuresis and urine examination epicystostomy was effected or both ureters were catheterized. All the experiments were carried out on an empty stomach of the animals.

Prior to introduction of bile into Wirsung's duct, background samples of blood, urina and pancreatic juice were taken for special enzymological investigations. After administration of bile into Wirsung's duct the same biological tests were carried out every hour until the experiment was completed. The activity of the following pancreatic enzymes was studied: α-amylase, lipase, total esterase activity, antitryptic activity.

Three dogs were used in the control group of the experiments. They were treated to induce an experimental pancreatitis only without administration of the hexapeptide according to the present invention; an acute experiment lasted for 6-8 hours, whereafter the dogs were slaughtered by intracardiac administration of hexenal.

30 minutes after the administration of bile into Wirsung's duct and then every 2 hours small pieces of pancreas tissue were taken from the animals from various sections for morphological investigations. In the second series of experiments 5 dogs were used. A hemorrhagic pancreonecrosis was induced in them and 2 hours after the development of acute pancreatitis an intravenous administration of the hexapeptide according to the present invention was started at the rate of 0.3 mg per kg of the animal's bodyweight. For enzymological and morphological studies the same biological samples and pieces of tissues of the pancreas were taken. The dogs were slaughtered 6-8 hours after the beginning of the experiment.

In the third series of experiments two dogs were used. The induced experimental pancreatitis was treated by means of the hexapeptide according to the present invention. The same tests were performed, but the dogs were not slaughtered. 24 hours from the beginning of the experiment and then 7 days and 15 days thereafter they were subjected to relaparotomy, the macroscopic view of pancreas was studied, pieces of the tissue of pancreas were taken for morphological studies.

The morphological studies of the pancreas in the control series of experiments (three dogs) have shown that for the chosen model of hemmorrhagic pancreonecrosis the major portion of exocrine cells is in the phase of an intensive synthesis and a continuous evolution of the pancreatic secretum accompanying by a complete disturbance of the secretory cycle. The lasting and continuous hyperfunction of the exocrine apparatus results in disturbance of the main function of acinar cells—production of secretum. For this reason, first observed is death of individual cells, a focal necrosis develops which becomes further propagated. The coming destruction of membrane structures of acinar cells is accompanied by penetration of active proteolytic enzymes into the interacinar space, development of broad destructive changes in the periacinar tissue and the formation of large-size regions of hemorrhages and steatonecroses.

After administration of infected bile into Wirsung's duct a focal pancreonecrosis with a pronounced interstitial edema develops within the immediate 30 minutes.

Two hours after introduction of infected bile into Wirsung's duct a diffusive hemorrhagic pancreonecrosis develops. This is mainly in the form of intralobular injuries of pancreas. When this pancreonecrosis is not treated, the scale of injury of exocrine parenchyma is extended and necrosis covers up to ⅔ or even entire lobules. A characteristic feature is a hemorrhagic impregnation of necrotic zones, edema and hemorrhages in interacinar spaces with pronounced disturbances in the system of microhemocirculatory bed—erythrostasis, aggregation of form elements and microthrombosises of capillaries and vanules.

4–6 hours after reproduction of pancreatitis the animals' pancreas macroscopically looks diffusive-edematic with single steatonecroses under the capsule and multiple inter- and intralobular hemorrhages.

Histologically the lobular pattern is disturbed due to large-size lobular and mosaic intralobular necroses. In the interlobular space a diffusive polymorphonucleic infiltration and large-size hemorrhages with precipitation of fibrin are observed in the case of venous and arterial plethora and lymphostasis. In necrotic zones extensive inter- and intraacinar, as well as perivascular hemorrhages are observed. In venules and capillaries erythrostases are revealed with hemolysis of erythrocytes, thrombostases with precipitation of fibrin and fibrinoid impregnation of vessel walls. In the zones of necrosis the pattern of acinuses is fully destroyed, only their individual outlines are retained due to the integrity of basal membranes. In lumens of such acinuses one may distinguish fragments of necrotized cells and individual laukocytes.

In the zones adjacent to those of necrosis there are intracellular and cellular necroses without segregation thereof from viable regions of the cytoplasm. Electron microscopy shows that in lumens of capillaries under endothelium and in cytoplasm of endotheliocytes precipitation of fibrin occurs which resulted in a partial of a complete destruction of a vascular wall when its integrity is ensured at the account of a fibrinoid impregnation of the structural elements of the wall. In cytoplasm of acinar cells with distrophic necrobiotic changes of organelles individual and multiple erythrocytes are determined.

In boundary zones of dead acinar cells a diffusive accumulation of zymogen granules is observed without signs of their extrusion into the duct. In such acinar cells there are large diffusive and focal necroses of elements of the granular reticulum without its segregation from the viable fragments of cytoplasm. A portion of acinar cells in the acinus are in the state of a complete necrosis. In such acinuses the integrity of cellular contacts is broken, cells are in the state of discomplexation and, in the form of individual cells of fragments, they freely penetrate into the interstice. These acinar cells retain their ability for secretum formation which is accompanied by the formation of large-size secretory vacuoles.

In the necrotic zones the integrity of cellular membranes is fully destroyed, organelles of acinar cells are represented by vacuolized membrane structures, nuclei are in the state of pyknosis or lysis with retention of clumps of a condensed chromatin amidst cellular detritus.

After treatment of animals with experimental hemorrhagic pancreonecrosis the character of parenchymatous necreosis is changed as compared to the control data. In the treatment of pancreonecrosis by the hexapeptide according to the present invention the absence of signs of hemorrhagic zones of necrosis and hemorrhages into the interstice is observed. The subcapsular and interlobular edema with defibration of connective structures. The inter- and intralobular vessels are anemic, their lumens are widened, vascular walls are unchanged.

In the zones of necrosis capillaries are fully retained. The latter are frequently dilated and plethoral. The inflammation infiltration is absent both in the zones of parenchymal necrosis and in the interlobular spaces.

In the zones of large-scale injuries, i.e. covering ½ or ⅓ of lobules still there are no clear-cut boundaries between the injured and unchanged parenchyma of the gland. In the zones of small-focus necroses a more clear boundary is observed between the injured parenchyma with minimal zones of distrophy. Outside the injury zones no signs of secretory activity are revealed, acinar cells are filled with a great amount of secretory granules and retain their ability if evolving secretum into the duct system.

One day after the treatment a positive dynamics is observed in the morphology of hemorrhagic pancreonecrosis. No signs of inter- and intralobular edema or inflammation in the interstice are noticed. Only in individual regions, in zones of unit steatonecroses a pronounced demarkation inflammatory torus and inflammatory infiltration are present which spread onto the adjacent interlobular spaces. Areactive steatonecroses are also observed.

Changes in the system of macro- and microhemocirculatory bed are absent.

The signs of a small-focal hemorrhagic pancreonecrosis are retained. A specific feature of the necrotic foci is their clear segregation from the non-injured parenchyma. The absence of necrotic detritus in small foci of the injury of retention thereof in large foci of injury with an insignificant inflammatory infiltration of those zones is observed. In certain foci of necrosis fresh hemorrhages are noticed. In the study of a secretory activity of the unchanged parenchyma a decline of synthesis and of the degree of filling of secretum are clearly revealed, distrophic changes are absent. The lumens of intralobular ducts are filled with secretum and modrately dilated. Therefore, in early stages of the treatment with hexapeptide according to the present invention the character of pancreonecrosis is changed, i.e. all morphological features characterizing progress of the process are absent; also absent are acute vascular changes such as stases, microthromboses. A coagulation type parenchymal necrosis prevails. The blood flow in the system of microcirculatory bed is retained both in the non-injured parenchyma and in zones of parenchymal necrosis which is especially important for a subsequent regeneration and elimination of necrotically changed tissues. The signs of disturbance of the drainage function of secretum along the duct system are retained, clear signs of decrease in the secretory activity of the unchanged acinar parenchyma are absent. Also absent are signs of dilation of centroacinar ducts and overfilling of ducts of various cross-sections with the secretum. Such changes point to the preservation of a normal drainage function of the duct system and ejection of secreted enzymes into the lumen of the duodenum.

One day after the treatment of an experimental pancreatitis by an intravenous administration of the hexapeptide according to the present invention, the pattern of a mixed pancreonecrosis is retained in the pancreas. In the majority of lobules there are large-size foci of necrosis without signs of hemorrhage or with a pronounced hemorrhagic impregnation of necrotic zones.

Changes in the system of micro-macro-circulatory bed—thromboses are absent, erythrostases are preserved.

In zones of large injuries, especially of hemorrhagic pancreonecrosis the signs of inflammation and clear-cut boundaries between the non-injured parenchyma are absent;

In small foci of injury necrotic detritus is retained and an insignificant polysegmentonucleic inflammatory infiltration is revealed.

In the gland there is revealed a clearly pronounced subcapsular and interlobular edema with focal hemorrhages into the interstice and a focal inflammatory infiltration. There are also large areas of fat necroses, mainly areactive ones or with a non-wide demarkation inflammatory torus.

The histochemical investigation of the pancreas has revealed a decrease in the secretory activity. The absence of distrophic changes outside the injured parenchyma, restoration of the secretion into the duct system is observed along with a certain disturbance of the drainage function of large ducts.

In the treatment of hemorrhagic pancreonecrosis with the hexapeptide according to the present invention a full organization of the necrosis foci is observed in the form of non-differentiated epithelial complexes or with the beginning of an acinar differentiation. The signs of inter- and intralobular sclerosis are absent. 14 days after the beginning of the treatment there occurs a complete regeneration of the acinar tissue with compensatory hyperfunction of acinary cells without any signs of an organ injury or inflammation, a pronounced trend is observed towards normalization of animolytic, lipolytic and proteolytic activity of the pancreas.

In the study of an acute toxicity of the hexapeptide according to the present invention it has been found that its $LD_{50}$ is 150 mg/kg. The hexapeptide according to the present invention does not change the cell formula of the blood, i.e. it does not inhibit the processes of homeopoiesis and does not cause pathological responses on the part of the immune system.

The effect of the hexapeptide according to the present invention was compared with that of widely employed preparations—5-fluorouracyl an d tracilol—on the same model of acute pancreatitis.

The employed dose of tracilol was 10,000 units per hour, the dose of 5-fluorouracyl—5 mg/kg; the dose of the hexapeptide according to the present invention was 0.3 mg/kg. It should be noted that the dose of 5-fluorouracyl causing death of 50% of the animals ($LD_{50}$) and constituting 750 mg/kg surpasses the therapeutic dose by 150 times, whereas in the case of the hexapeptide according to the present invention its $LD_{50}$ surpasses the therapeutic dose by 500 times.

In the early stages of treatment with 5-fluorouracyl a noticeable inflammatory infiltration of necrotic zones and of the interstice is retained.

In later stages of the treatment the scale of necrosis of the exocrine tissue is decreased, but a large-size infiltration of the interstice is retained; appearance of a plurality of foci of fat pancreonecrosis with a leukocytic torus (the process occurs according to the microabscessing type) and development of initial phenomena of sclerosis of interstice are observed. 7 days after the beginning of the treatment a pronounced fibrosis of the pancreas with breaking of lobules into fragments is developed. Regeneration of the pancreas is incomplete, since the development of a non-differentiated epithelial tissue takes place.

In the treatment of an experimental acute pancreatitis with tracilol in the early stages of the treatment a progressing hemorrhagic necrosis is observed along with a hemorrhagic inbibition of the interstice and necrotic zones. Tracilol diminishes disturbances of the intra-organ microhemolymphocirculation, in individual experiments it eliminates vascular thromboses; however, the animals die within 8–10 hours after the beginning of the experiment due to a progressing necrosis of the exocrine parenchyma and enzymatic toxemia.

The results of the performed tests are shown in Tables 1 to 3 hereinbelow.

TABLE 1

Changes of enzymatic activity in blood serum in experimental hemorrhagic pancreonecrosis after an intravenous administration of tracilol in the dose of 10,000 units/hour (3 dogs)

| No. | Measured parameters | Values in the case of developed pancreonecrosis | Values after administration of tracilol after | |
|---|---|---|---|---|
| | | | 4 hours | 6 hours |
| 1. | Activity of alpha-amylase, mg/h · ml | 152.0 ± 18.2 | 144.2 ± 16.0 | 158.0 ± 15.3 |
| 2. | Activity of lipase, units | 0.62 ± 0.04 | 2.04 ± 0.06 | 2.26 ± 0.81 |
| 3. | Total esterase activity, μM/ml | 0.64 ± 0.03 | 0.72 ± 0.08 | 0.78 ± 0.09 |
| 4. | Antitryptic activity, IU | 22.0 ± 0.2 | 20.2 ± 0.08 | 18.0 ± 2.6 |

TABLE 2

Variation of enzymatic activity in blood serum in experimental hemorrhagic pancreonecrosis after an intravenous administration of 5-fluorouracyl in the dose of 5 mg/kg (3 dogs)

| No. | Measured parameters | Values for the developed pancreo-necrosis | Values after administration of 5-fluorouracyl after | |
|---|---|---|---|---|
| | | | 4 hours | 6 hours |
| 1. | Activity of alpha-amylase, mg/h · ml | 158.0 ± 18.2 | 152.2 ± 24.1 | 153.3 ± 17.1 |
| 2. | Activity of lipase, units | 0.62 ± 0.12 | 0.48 ± 0.02 | 0.54 ± 0.08 |
| 3. | Total esterase activity, μM/ml | 0.58 ± 0.07 | 0.56 ± 0.02 | 0.58 ± 0.04 |
| 4. | Antitryptic activity, IU | 22.2 ± 1.4 | 20.1 ± 1.2 | 20.1 ± 1.2 |

TABLE 3

Variation of enzymatic activity in blood serum in experimental hemorrhagic pancreonecrosis after an intravenous administration of the hexapeptide according to the present invention in the dose of 0.3 mg/kg (7 dogs)

| No. | Measured parameters | Values for the developed pancreo-necrosis | Values after administration of the hexapeptide of this invention, after | |
|---|---|---|---|---|
| | | | 4 hours | 6 hours |
| 1. | Activity of alpha-amylase, mg/n · ml | 178 ± 28.2 | 246.2 ± 26.7 | 258.2 ± 33.2 |
| 2. | Activity of lipase, units | 1.15 ± 0.03 | 0.25 ± 0.02 | 0.40 ± 0.05 |
| 3. | Total esterase activity, μM/ml | 0.76 ± 0.05 | 0.16 ± 0.08 | 0.20 ± 0.09 |
| 4. | Antitryptic activity, IU | 26.5 ± 1.3 | 78.0 ± 13.1 | 72.0 ± 2.5 |

As it follows from the data shown in the foregoing Tables 1 to 3, the hexapeptide according to the present invention has essential advantages over 5-fluorouracyl and tracilol as regards it effect on the characteristics of activity of enzymes in blood serum under conditions of a developed pancreonecrosis. Thus, upon administration of the hexapeptide according to the present invention activity of lipase is sharply reduced, the total esterase activity of blood is lowered and a three-time increase of the antitryptic activity is noticed. This points to a lowered ejection of active pancreatic enzymes into blood simultaneously with elevation of the level of their inhibitors. Upon administration of 5-fluorouracyl these characteristics remain substanctially unchanged, whereas infusions of tracilol do not prevent from a progressing increase of activity of lipase and esterases.

Therefore, the hexapeptide according to the present invention in the case of acute pancreatitis effectively inhibits synthesis of pancreatic enzymes, improves intra-organ blood- and lymphocirculation, limits the area of necrotic changes of the exocrine parenchyma and, upon repeated parenteral administrations, results in a complete regeneration of the pancreas without any residual signs of necrosis and inflammatory phenomena.

The hexapeptide according to the present invention, i.e. Tyrosyl-alanyl-glycyl-phenylalanyl-leucyl-arginine is synthetically prepared by way of a successive building-up of a peptide chain on one amino acid, starting with arginine in the form of a free base and activated esters of protected amino acids.

For a better understanding of the present invention, the following specific example illustrating preparation of the hexapeptide of this invention is given hereinbelow.

EXAMPLE 1.74 g (10.00 mM) of arginine are suspended in 25 ml of dimethylformamide, the solution is added with 4,25 g (11.00 mM) of p-nitrophenyl ester of carbobenzoxy-glycine, the mixture is stirred at room temperature for one day. Dimethylformamide is evaporated, the residue is dissolved in 5 ml of methanol and added with 300 ml of ether. The resulting precipitate is filtered-off, washed with ether on the filter and dried in a vacuum desiccator to give 4.05 g (96%) of carbobenzoxy-leucyl-arginine, m.p. 126°-130° C.

$R_f^1$ 0.46 (n-butanol:acetic acid:water 4:1:5) (A);
$R_f^2$ 0.63 (n-butanol:pyridine:acetic acid:water 10:5:6:1:7.5) (B);
$R_f^3$ 0.74 (n-butanol:acetic acid:water 3:1:1) (C);
$[\alpha]_D^{20} = -13°$ (cI, MeOH).

4.05 g of carbobenzoxy-leucyl-arginine (9.61 mM) are dissolved in 35 ml of trifluoroacetic acid and a current of dry hydrogen bromide is passed through the resulting solution for one hour. The solvent is evaporated, the residue is added with 150 ml of ester, the precipitate is filtered-off, dissolved in water and treated with an ion-exchange resin Amberlite IR A-410 (OH$^-$form) till a negative reaction on bromine ions). The resin is filtered-off, washed on the filter with methanol, water; the filtrate is evaporated, residual amounts of water are removed by an azeotropic distillation with isopropanol. The residue is dissolved in 25 ml of dimethylformamide, the solution is added with 4.44 g (10.58 mM) of p-nitrophenyl ester of carbobenzoxy-phenylalanine. The reaction mixture is allowed to stand for one day at room temperature. Dimethylformamide is evaporated, the residue is dissolved in 5 ml of methanol and added with 300 ml of ether. The resulting precipitate is filtered-off, washed on the filter with ester and drined in a vacuum desiccator to give 4.43 g (81%) of carbobenzoxy-phenylalanyl-leucyl-arginine, m.p. 133°-136° C.; $[\alpha]_D^{20} = -19.3$ (cI, MeOH). $R_f^1=0.71$ (C), $R_f^2=0.66$ (B), $R_f^3=0.63$ (ethylacetate:pyridine:acetic acid:water 45:20:6:11) (D).

From 4.43 g (7.79 mM) of carbobenzoxy-phenylalanyl-leucyl-arginine and 2.83 g (8.75 mM) of p-nitrophenyl ester of carbobenzoxy-glicine, in a manner similar to that described hereinabove, 4.14 g (85%) of carbobenzoxy-glycyl-phenylalanyl-leucyl-arginine with melting point of 140°-143° C. are obtained.

$[\alpha]_D^{20} = -14.8$ (cI, MeOH); $R_f^1=0.48$ (C), $R_f^2=0.50$ (A), $R_f^3=0.60$ (B).

From 0.63 g (1.01 mM) of carbobenzoxy-glycyl-phenylalanyl-leucyl-arginine and 0.38 g (1.11 mM) of p-nitrophenyl ester of carbobenzoxy-alanine, in a manner similar to that described hereinbefore, 0.56 g (79%) of carbobenzoxy-alanyl-glycyl-phenylalanyl-leucyl-arginine with m.p. of 147°-149° C. is obtained. $[\alpha]_D^{25} = -4.0$ (c 0.5, dimethylformamide). $R_f^1=0.33$ (C), $R_f^2=0.35$ (D), $R_f^3=0.67$ (chloroform:methanol: 32% acetic acid 60:45:20) (E).

From 0.56 g (0.80 mM) of carbobenzoxy-alanyl-glycyl-phenylalanyl-leucyl-arginine and 0.43 g (0.88 mM) of p-nitrophenyl ester of carbobenzoxy-o-benyl-tyrosine in a manner similar to that described hereinbefore 0.64 g (84%) of carbobenzoxy-o-benzyl-tyrosyl-anyl-glycyl-phenylalanyl-leucyl-arginine with the melting point of 150°–153° C. is obtained. $[\alpha]_D^{25} = -8.1$ (cI, dimethylformamide). $R_f^1 = 0.41$ (C); $R_f^2 = 0.53$ (D), $R_f^3 = 0.60$ (n-butanol:pyridine:conc.ammonia:water 20:12:3:15) (F).

0.64 g (0.67 mM) of carbobenzoxy-o-benzyl-tyrosyl-alanyl-glycyl-phenylalanyl-leucyl-arginine is dissolved in 20 ml of acetic acid with the addition of anisol (30% by volume) and hydrogenated in the presence of a palladium catalyst. The catalyst is filtered-off, washed on the filter with acetic acid, the filtrate is evaporated, the residue is reprecipitated from methanol (5 ml) with ester (150 ml), dried in a vacuum desiccator. The resulting product is placed into a column (600×15) with Sephadex SP C-25 and fractionated in a gradient of a pyridine-acetate buffer of 0.05–1.00M.

In this manner 0.34 g (65%) of tyrosyl-alanyl-glycyl-phenylalanyl-leucyl-arginine with the melting temperature of 173°–176° C. is obtained. $[\alpha]_D^{22} = -19.1$ (c 0.33, H$_2$O). $R_f^1 = 0.55$ (E), $R_f^2 = 0.41$ (F), $R_f^3 = 0.54$ (B).

Data of aminoacid analysis: tyrosine 1.18 (I), alanine 1.17 (I), glycine 1.15 (I), phenyl-alanine 1.00 (I), leucine 0.99 (I), arginine 1.09 (I).

Individuality of the produced compound is justified by the NMR-spectrum (FIG. 1), as well as by the method of a highly effective liquid chromatography. The peptide was eluted by a single peak at 42.3% of the gradient on the 14.9-th minute. (Column 250×4.6 mm, Spherisorb ODS 5$\mu$; mobile phase A: 0.05M KH$_2$PO$_4$; pH 3.0; B:CH$_3$CN; Gradient: 20%→50% B for 20 min; pressure 1,500 psi, rate 1 ml/min; detection at 214 nm).

INDUSTRIAL APPLICABILITY

The hexapeptide according to the present invention exhibits an antipancreonecrotic activity and can be useful in medicine for the treatment of an acute pancreatitis.

We claim:

1. A hexapeptide of the following structure:

Tyr-Ala-Gly-Phe-Leu-Arg.

* * * * *

UNITED STATES PATENT AND TRADEMARK OFFICE
CERTIFICATE OF CORRECTION

PATENT NO. : 4,695,622
DATED : September 22, 1987
INVENTOR(S) : Evgeny Ivanovich Chazov et al It is certified that error appears in the above-identified patent and that said Letters Patent is hereby corrected as shown below:

Title Page, Column 1,

[22] "PCT Filed: April 24, 1987"

should read -- PCT Filed: April 24, 1985 --.

Signed and Sealed this

Twenty-second Day of March, 1988

Attest:

DONALD J. QUIGG

*Attesting Officer*     *Commissioner of Patents and Trademarks*